United States Patent [19]
Anderson

[11] Patent Number: 5,410,472
[45] Date of Patent: Apr. 25, 1995

[54] METHOD FOR CONDITIONING OR REHABILITATING USING A PRESCRIBED EXERCISE PROGRAM

[75] Inventor: Stephen T. Anderson, North Oaks, Minn.

[73] Assignee: ErgometR$_x$ Corporation, St. Paul, Minn.

[21] Appl. No.: 967,357

[22] Filed: Oct. 27, 1992

Related U.S. Application Data

[63] Continuation-in-part of Ser. No. 702,136, May 13, 1991, which is a continuation of Ser. No. 319,262, Mar. 6, 1989, abandoned.

[51] Int. Cl.$^6$ .............................................. G06F 15/00
[52] U.S. Cl. ............................... 364/413.04; 128/707; 482/5; 482/9; 482/900; 601/1
[58] Field of Search .................... 364/413.04; 272/7.3, 272/DIG. 6, 96; 128/25 R, 25 B; 235/379; 482/5, 900, 902

[56] References Cited

U.S. PATENT DOCUMENTS

| | | | |
|---|---|---|---|
| 3,744,480 | 7/1973 | Gause et al. | 128/2.06 R |
| 3,848,467 | 11/1974 | Flavell | 272/DIG. 6 |
| 4,082,267 | 4/1978 | Flavell | 272/125 |
| 4,244,021 | 1/1981 | Chiles, III | 272/DIG. 6 |
| 4,261,562 | 3/1981 | Flavell | 272/DIG. 6 |
| 4,408,613 | 10/1983 | Relyea | 128/670 |
| 4,463,764 | 8/1984 | Anderson et al. | 128/719 |
| 4,628,910 | 12/1986 | Krukowski | 128/25 R |
| 4,642,769 | 2/1987 | Petrofsky | 272/DIG. 6 |
| 4,750,738 | 6/1988 | Dang | 272/125 |
| 4,786,049 | 11/1988 | Lautenschlager | 272/73 |
| 4,790,528 | 12/1988 | Nakao et al. | 272/73 |
| 4,822,036 | 6/1989 | Dang | 272/129 |
| 4,842,274 | 6/1989 | Oosthuizen et al. | 272/129 |
| 4,869,497 | 9/1989 | Stewart et al. | 272/129 |
| 5,054,774 | 10/1991 | Belsito | 272/DIG. 6 |
| 5,230,673 | 7/1993 | Maeyama et al. | 482/5 |

FOREIGN PATENT DOCUMENTS 2187554 9/1987 United Kingdom .

OTHER PUBLICATIONS

Fox, Edward et al, "The Physiologic Basis for Exercise and Sport", William C. Brown Communications, Inc., Dubuque, Iowa (1989, 1993), p. 294.

Sherill, D. L. et al, "Computer-controlled cycle ergometer", *IEEE Trans. on Biomed. Eng.*, vol. BME-28, No. 10, Oct. 1981, 711-13.

Russell, J. C. et al, "Dynamic torquemeter calibration of bicycle ergometer", *J. Appl. Physiol.*, vol. 61, No. 3, Sep. 1986, 1217-20.

McCartney, N. et al, "Torque-velocity relationship in isokinetic cycling exercise", *J. Appl. Physiol.*, vol. 58, No. 5, May 1985, 1459-62.

McCartney, N. et al, "A constant-velocity cycle ergometer for the study of dynamic muscle function", J. Appl. Physiol., vol. 55, No. 1, Jul. 1983, 212-17.

Casaburi, Richard et al, "Reductions in Exercise Lactic Acidosis and Ventilation as a Result of Exercise Training in Patients with Obstructive Lung Disease", *Am Rev. Respir Dis*, No. 143, 1991, pp. 9-18.

Coplan, Neil L. et al, "Using Exercise Respiratory Measurements to Compare Methods of Exercise Prescription", *Am J. Cardiol*, No. 58, 1986, pp. 832-836.

*Primary Examiner*—Gail O. Hayes
*Assistant Examiner*—Frantzy Poinvil
*Attorney, Agent, or Firm*—Haugen and Nikolai

[57] ABSTRACT

A distributive method of physical rehabilitation and conditioning using an ergometer on which exercise protocols or workouts are performed by a subject is described. The intensity and duration of the workouts are defined as the independent variables and physiological and psychological variables are measured and treated as dependent variables. The exercise protocol is stored on a portable medium and the exercise program further defines a series of successive exercise sessions conducted over time in which the same exercise protocol is repeatedly performed by the subject; and, during the performance of which protocol, physiological and psychological variables are measured. The relative changes in one or more of the dependent variables which occur over the course of the series of sessions of the exercise training program measure progress and provide the basis for modification of the exercise protocol for the next exercise training program for that subject.

19 Claims, 10 Drawing Sheets

| RPE | DAY N | | DAY 4 | DAY 3 | DAY 2 | DAY 1 |
|---|---|---|---|---|---|---|
| SAMPLE 1 | 0 | | 0 | 0 | 0 | 0 |
| SAMPLE 2 | 2 | | 3 | 3 | 4 | 4 |
| SAMPLE 3 | 2 | | 3 | 4 | 5 | 4 |
| SAMPLE 4 | 3 | | 4 | 5 | 5 | 5 |
| SAMPLE 5 | 4 | | 4 | 5 | 6 | 7 |
| SAMPLE 6 | 4 | | 5 | 5 | 7 | 8 |

| HEART RATE | DAY N | | DAY 4 | DAY 3 | DAY 2 | DAY 1 |
|---|---|---|---|---|---|---|
| SAMPLE 1 | 75 | | 80 | 82 | 88 | 92 |
| SAMPLE 2 | 88 | | 92 | 95 | 100 | 112 |
| SAMPLE 3 | 115 | | 120 | 120 | 125 | 130 |
| SAMPLE 4 | 125 | | 127 | 133 | 136 | 138 |
| SAMPLE 5 | 130 | | 136 | 138 | 140 | 145 |
| SAMPLE 6 | 130 | | 136 | 140 | 144 | 148 |

METHOD FOR CONDITIONING OR REHABILITATING USING A PRESCRIBED EXERCISE PROGRAM

CROSS-REFERENCE TO RELATED APPLICATION

This is a continuation-in-part of application Ser. No. 07/702,136 filed May 13, 1991, which in turn is a continuing application of Ser. No. 07/319,262 filed Mar. 6, 1989, now abandoned.

BACKGROUND OF THE INVENTION

I. Field of the Invention

This invention relates generally to the field of physical exercise performed in accordance with a prescribed training program, and more particularly, to a method for effectively utilizing the measured aerobic capacity of a subject to develop, monitor progress using, and accordingly modify an exercise training program, using an ergometer to optimally achieve an increase in the size of the physical training effect to more effectively motivate the subject to complete the exercise training program, and to reduce the cost of providing exercise training programs.

II. Discussion of the Prior Art

It is well-recognized that physical exercise can be used to increase the physical well being of individuals whose health ranges from that of being simply "out of shape" to that of having some form of hemodynamic or respiratory dysfunction. However, it is also known that whereas over-exertion can be dangerous and even life-threatening, exercise below a certain intensity may prove to be ineffective in improving exercise tolerance.

Various forms of exercise machines are known in the art. Devices of the class commonly referred to as ergometers are adapted to allow a user to work against a force and to displace that force through a distance, i.e., perform work. Devices of the class include stair-climbing machines, treadmills, and the like. Typical of such devices is the so-called bicycle ergometer in which the user pedals a stationary device so as to drive a flywheel. The amount of effort expended is determined by the mass of the flywheel as well as the setting of friction pad brakes normally coacting with the flywheel.

Ergometers which use an electrically controllable element to directly assist or resist the force applied by the user and to dissipate the energy applied by the user are known. These include computer-controlled, motor-assisted cycle ergometers which can provide a dynamic range of power dissipation. One such device that controls the armature field current to determine power dissipation over a range between 0 and 350 watts at a constant 60 rpm pedaling speed is described by Sherrill et al, IEEE Trans on Bio-Med Engineering, Volume BME 28, No. 10 (1987). That system is calibrated at a certain speed or speeds and is not accurate at speeds other than those for which it is calibrated so that it does not allow the operator to independently select the most comfortable pedaling rate. A torque/speed related feedback control system is described in Gause et al (U.S. Pat. No. 3,744,480). That system has a manual set-point in the direct work measuring mode.

Further, U.S. Pat. Nos. 4,261,562; 4,082,267; 3,848,467; 4,822,036; and 4,750,738 all disclose the use of a dynamoelectric machine such as an electric motor or generator for controlling the speed of the apparatus and dissipating the energy input by the user. U.S. Pat. No. 4,842,274 to Oosthuizen et al discloses a variant of this approach in which an hydraulic clutch is interposed between the dynamoelectric machine and the movable element of the apparatus. It is further known to control the operation of a motor-assisted cycle ergometer device based on work as related to a target or programmed heart rate in relation to the observed real time heart rate of the operator. Such a programmable control system is also disclosed by Gause et al in the above-cited U.S. Pat. No. 3,744,480. Nakao et al (U.S. Pat. No. 4,790,528) describe a rehabilitation training device in the form of a motor-assisted cycle ergometer which is controlled in a manner such that the pedaling resistance load is varied based on the actual monitored heart rate of the operator in relation to a target value.

An ideal example of an ergometer usable with the present invention has been described by Boyd in co-pending patent application Ser. No. 07/801,252. In that device, the actual energy imparted by the user into the system is measured and compared to a setpoint. The resistance can then be varied so that the actual energy input of the exerciser matches that specified by the setpoint, independent of the speed of pedaling by the exerciser.

All of these prior devices are designed to monitor or control one aspect of an exercise training program. Ergometers of all varieties simply vary the resistance to the exerciser in some fashion so that energy can be expended by the exerciser according to an establish setpoint and absorbed by the ergometer.

Cardiopulmonary exercise stress tests have long been used to measure aerobic capacity. A cardiopulmonary exercise stress testing system, of course, simply measures oxygen consumption ($VO_2$), carbon dioxide production ($VCO_2$), ventilation (VE), heart rate (HR) and blood pressure (BP); and from those measurements, one can derive maximum aerobic capacity ($VO_2$ max) and an exhaustion index (anaerobic threshold) of a subject.

A further multi-function cardiopulmonary exercise system is shown in Anderson et al (U.S. Pat. No. 4,463,754). That system includes a microprocessor-based waveform analyzer for performing a real time breath-by-breath analysis of cardiopulmonary activity to measure a plurality of parameters including stress testing for diagnosing and to ascertain physical fitness. While this device is an excellent source of evaluation data, it clearly does not function as a training or rehabilitation system.

Presently, these are used independently and there is no link between the physiologic measurements of aerobic fitness—$VO_2$ max and anaerobic threshold—and the tools of physical training— ergometers. The importance of such a linkage has received increasing attention in the medical literature. It is known that exercise training stimulates changes in the exercising muscles, which increase capillary density, the number of mitochondria, and the concentration of aerobic enzymes. These changes act to increase the capacity for aerobic work and forestall the onset of lactic acidosis. Casaburi et al have reported that an exercise program in which subjects are exercised at workrate intensities at or above the workrate intensity at which the anaerobic threshold occurs can achieve a marked improvement in aerobic capacity. "Reductions in Exercise Lactic Acidosis and Ventilation as a Result of Exercise Training in Patients with Obstructive Lung Disease", (*Am Rev Respir Dis,* 1991; 143:9–18). In another study by Coplan et al, "Using Exercise Respiratory Measurements to Compare Methods of Exercise Prescription" (*Am J Cardiol*, 1986; 58:832–836), it was stated that exercise prescriptions based upon anaerobic threshold are preferable to exercise prescriptions based upon predicted maximal heart rate. It is well established that sustained exercise at intensities approaching the work rate intensity at $VO_2$ max is impossible, and possibly dangerous.

From the above, it will readily be observed, then, that workrate, in fact, is the independent variable of both a cardiopulmonary stress test and of an exercise training program, and that the dependent physiological variables including workrate, oxygen uptake or consumption ($VO_2$), carbon dioxide production ($VCO_2$), ventilation (VE), heart rate (HR) and blood pressure (BP), will remain unchanged unless exercise training is used to effect change. Moreover, it becomes apparent that using HR, for example, as a physiologic setpoint to control the workrate, or exercise intensity, of an ergometer clearly does not logically follow. In other words, the scientific method does not teach the use of a dependent variable (HR) to control the value of an independent variable (workrate). In accordance with the present invention, a more rational approach, and one that more closely adheres to the scientific method, is one that uses workrate as the independent variable of an exercise training program and the dependent physiologic variables as measurements of the efficacy of the exercise training program.

Moreover, to insure efficacy of an exercise training program, aspects other than purely physiologic factors need to be taken into account when designing a protocol for and measuring the achievements resulting from the exercise training program. It is important that the physician or medical professional be provided with sufficient data to fairly assess patient compliance with the program and the psychological acceptability of the exercise protocol. The many factors involved in properly gauging the success of the exercise training program, heretofore, has required that the exercise program be carried out in a health provider's office or clinic where the intensity of exercise could be adjusted while the physiologic, psychologic, and compliance factors could be directly observed. This, of course, greatly increases the cost of implementing the exercise training program.

While both the techniques and tools exist for implementing an exercise training program which can be both productive and safely tolerated by the exercising subject, no satisfactory method, or tools to implement the method, has been available for (1) producing an exercise training protocol for an ergometer which can be faithfully reproduced by the subject, independent of his pedal speed, (2) providing an off-line monitoring capability for the prescribing physician or medical professional to determine exercise protocol compliance and to determine the physiologic and psychologic adaptation of the subject to the protocol, (3) providing relevant, easy to understand information to the exercising subject to visualize the achievements the subject is making during the training program so as to better motivate the subject to continue the exercise training program to completion, and (4) increasing, or decreasing, the duration and/or intensity of the exercise training protocol over time as a function of measured and monitored physiologic and psychologic variables.

As used herein, the term "protocol" refers to the programmed variation of a target workrate over a predetermined exercise time period used for repeated sessions in an exercise program which, in turn, consists of a predetermined number of such sessions over a program time period. The preferred protocol is in the form of a two-dimensional array of values where one dimension is workrate and the other dimension is time. A protocol can be displayed as either a table of numbers or as a graphical plot. The preferred method is by presenting the protocol as a graphical plot of workrate v. time. A display of this type is believed easier to interpret and understand.

OBJECTS

It is accordingly a principal object of the present invention to provide an improved method of developing and monitoring an exercise training program.

Another object of the invention is to provide a method by which an exercise training program can be optimally designed using measured cardiopulmonary data of a subject to define a training window of upper and lower exercise intensity.

Yet anther object of the invention is to provide a graphical method involving a personal computer resident software program to easily define an exercise protocol which recognizes a subject's personal training window and which can be used to establish the duration of exercise and to produce a known amount of energy expenditure.

Still another object of the invention is to provide a method involving a personal computer resident software program to define monitoring times for exercise variables to provide feedback on subject compliance, physiologic adaptation, and psychologic adaptation to the exercise protocol.

A further object of the invention is to provide a method and apparatus for executing an exercise training program wherein the subject is constrained to follow a predefined intensity vs. time protocol but in which the subject's pedal frequency is not constrained.

A still further object of the invention is to provide an exercise training program in which a desired exercise protocol is first recorded on a portable machine readable medium and then that medium is used to control the exercise intensity to be performed by a subject on an ergometer such that the actual intensity performed will comply with the predefined protocol.

A yet still further object of the invention is to provide a method of monitoring, in an off-line fashion, an exercise training program in which a desired exercise monitoring protocol is first recorded on a machine readable medium and then that medium is used to control the sampling of exercise variables from the subject while exercising on an ergometer.

Yet still another object of the invention is to provide a method of reporting on the compliance of a subject to an exercise training program.

Yet another object of the invention is to provide a method of reporting on the physiologic adaptation of a subject to an exercise training program.

It is also an object of the invention to provide a method of reporting on the psychologic adaptation of a subject to an exercise training program.

The foregoing as well as other objects and advantages of the invention will become apparent to those skilled in the art from the detailed description (below) of a preferred embodiment, especially when considered in conjunction with the accompanying drawings.

SUMMARY OF THE INVENTION

The present invention, to a large extent, obviates all of the foregoing problems. The present invention concerns a different philosophical approach to physical rehabilitation and conditioning in which the intensity (workrate) and duration (time) of the workout are defined as independent variables for an exercise protocol, and the subject's exercise training program is defined as a series of exercise sessions over time wherein the same exercise protocol is repeatedly used by the subject. Compliance, physiologic response and psychologic response to the prescribed exercise training program are measured during the exercise training sessions and are treated as dependent variables of the intensity-time function. In this manner, relative changes (generally improvements) in the dependent variables which occur as a result of the exercise training program can be measured.

In accordance with the preferred method, a cardiopulmonary exercise stress test is performed to determine the subject's exercise tolerance using one or more of many accepted measurements such as those defined by respiratory exchange ratio ($R=1$), ventilatory threshold (VT), anaerobic threshold (AT) and $VO_2$ max. The workrates at which these physiological limitations occur are noted and are used together with other observations as the basis for developing an initial exercise protocol and program.

The protocol is preferably developed using a graphic display grid and cursor, possibly using well-known rubber banding techniques, on a personal computer or the like with a compatible resident software program. The exercise protocol is developed by the exercise programmer who typically is either a physician or other medical professional such as an exercise physiologist. The medical professional then puts together, edits on screen and finalizes the workout protocol graphically using the cursor or mouse to move a line to define workrate over time as he sees fit. This is normally coordinated with a digitized "snap to" grid in the program. In this manner, any protocol of any duration or complexity can be easily formed.

Once the protocol itself is defined, dependent physiological and psychological variables to be monitored and measurement sampling rates are inserted in the program. The physiological variables are selected from oxygen consumption ($VO_2$), carbon dioxide production ($VCO_2$), ventilation (VE), heart rate (HR) and blood pressure (BP), and psychological variables include degree of compliance with the regimen and rate of perceived exertion (RPE).

Once generated, the resulting exercise protocol and monitoring protocol are then recorded into the database of the subject on the system disc of the PC and together with instructions for the subject onto a transportable form of recording media such as a floppy disc or data key. The transportable form of recording medium is designed to be used with any compatible ergometer under the control of a separate microcontroller in a PC or microcomputer controlled system.

According to the invention, the subject follows the same workout protocol for a predetermined number of repetitive sessions which make up the program and, while the subject is exercising, information is obtained and stored back into the transportable media device for later use. Feedback may be obtained in the form of a printed report of the recorded daily use using software comprising another PC resident program. After the subject is finished with the number of sessions in accordance with the exercise program, the data key or other portable recording media is returned to the original, or possibly a different, programmer for evaluation. Changes in the relevant dependent variable, such as a reduction of heart rate, which show improved conditioning are utilized by the programmer to either declare the need for the regimen at an end or to make modifications in the original protocol to be used for a next program of successive sessions.

BRIEF DESCRIPTION OF THE DRAWINGS

In the drawings, in which like numerals in the several views refer to corresponding parts.

DETAILED DESCRIPTION

According to one aspect of the invention, the particular form of mechanical or electromechanical ergometer device used in the practice of the method is not limiting as long as the exercise machine employed has the ability to allow proper implementation of that method. It is further important to note that the operation of an ergometer device likewise forms but a part or segment of the much broader concept that the present invention includes. For example, the above-referenced Boyd application details an ergometer viably compatible with the present invention, the details of which can be incorporated herein as required for a more detailed example of the device described next below with reference to FIGS. 1-3.

Figure 1:
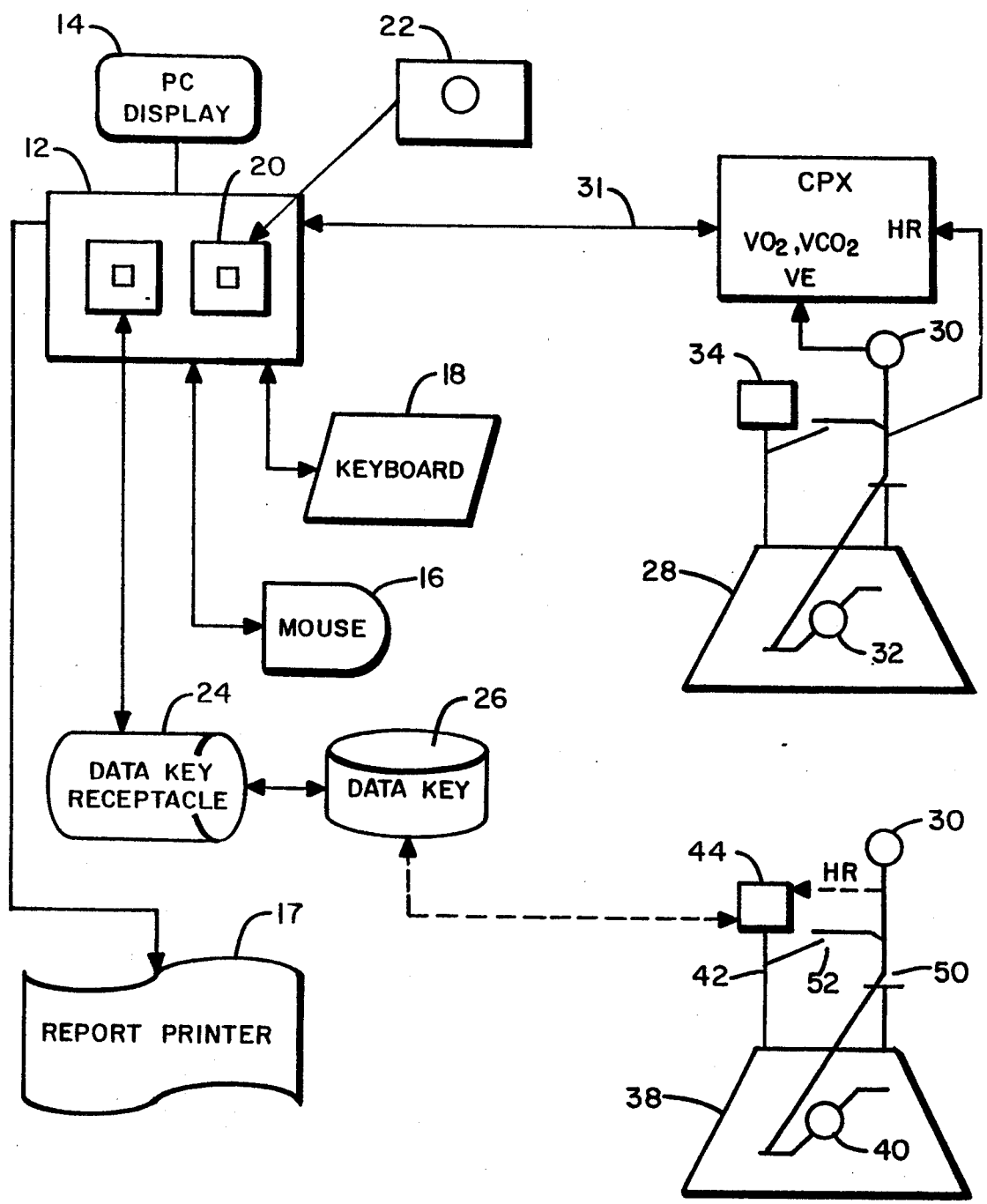
FIG. 1 is a schematic drawing of system hardware characteristically used in carrying out the method of the present invention.

Referring first to FIG. 1, there is illustrated the basic equipment whereby the method of the present invention may be employed to develop an exercise program in accordance with a predetermined protocol and thereafter execute the program. The system is seen to include a data processing device, here shown as a personal computer or PC 12 which comprises a video display terminal 14 with associated mouse 16, report printer 17 and a keyboard 18. The system further has a floppy disc handler 20 with associated floppy disc 22, a data key input/output interface device is shown at 24 and a data key at 26. As is well known in the art, the floppy-disc handler 20 and data key input/output interface device 24 comprise read/write devices for reading prerecorded information stored, deleting, adding or changing recorded information, on a machine-readable medium, i.e., a floppy disc, and for providing signals which can be considered as data or operands to be manipulated in accordance with a software program loaded into the RAM or ROM memory (not shown) included in the computing module 12.

The equipment used to develop the predetermined protocol includes a bicycle ergometer designed for use in a cardiopulmonary stress testing system (CPX) as is represented at 28 together with a subject 30 operating a pedal crank input device 32. A graphic display device 34 interfaces with the subject during operation of the CPX device. Data in the form of stress dependent physiological and psychological variables are measured or evaluated. The physiological variables may be selected from blood pressure (BP), heart rate (HR), ventilation (VE), rate of oxygen uptake or consumption ($VO_2$) and carbon dioxide production ($VCO_2$) or other recognized variables. The psychological variables include the degree of compliance or attempted compliance with the requested regimen or protocol and more subjective criteria such as the relative rate of perceived exertion (RPE). Physiological data collected is fed into the computing module 12 via a conductor 36 for use in developing the protocol to be contained on the data key 26.

Figure 3:
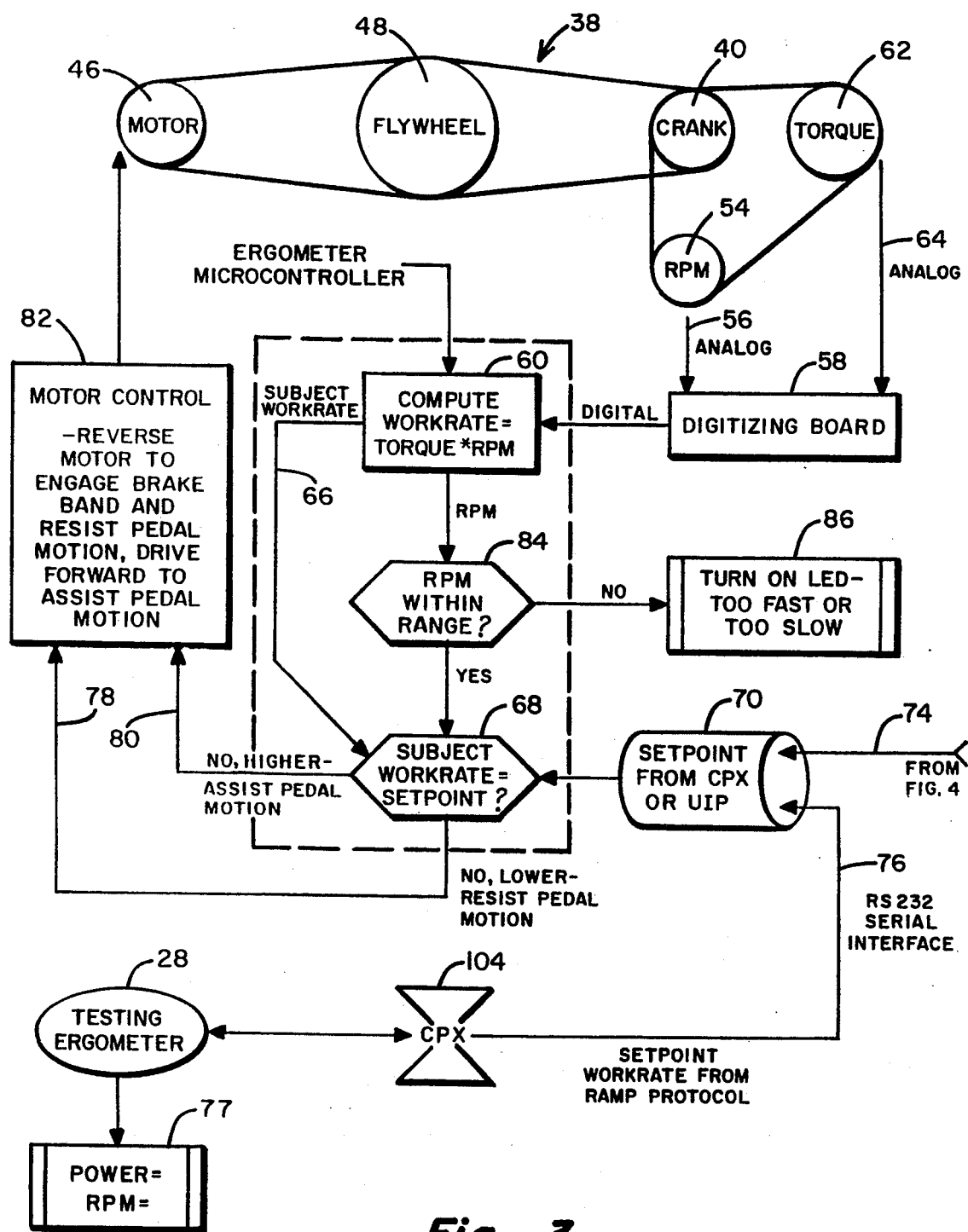
FIG. 3 is a functional block diagram and flow chart of the ergometer of FIG. 1.
Figure 4:
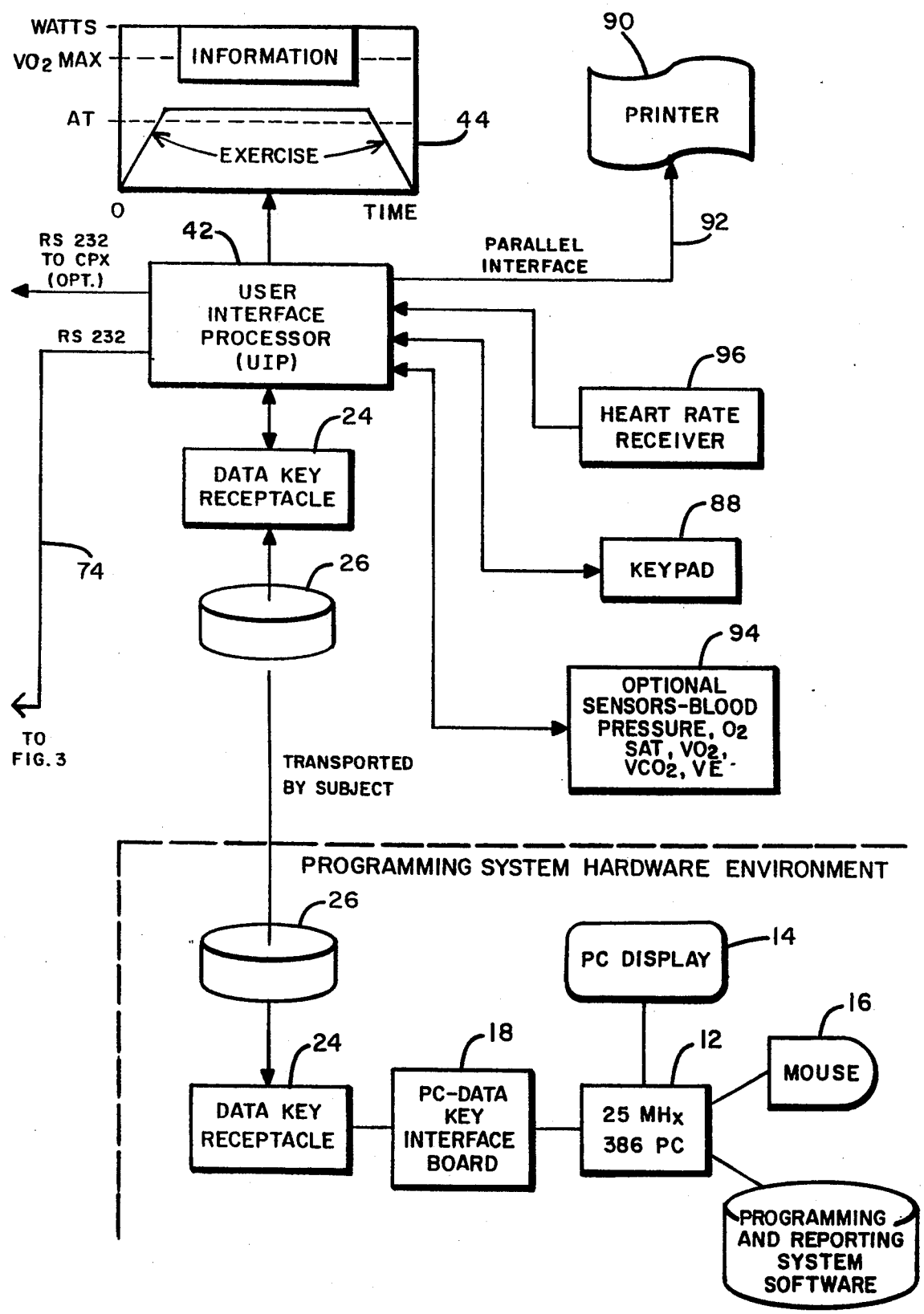
FIG. 4 illustrates by means of a schematic block diagram the ergometer and programming system hardware.

The equipment used in carrying out the protocol developed initially using the CPX in accordance with the present invention also includes an ergometer device 38 with input pedal crank 40. The system further includes a User Interface Processor (or UIP) 42 (FIG. 4) and an associated graphics display at 44. More complete flow chart details of the exercise ergometer system are depicted in FIGS. 3 and 4. It will be recognized that the present invention is not directed to the exercise device itself. The representations of one type of equipment that can be used in carrying out the method of the present invention are in no way intended to limit the scope of the invention. It should be noted that details of the mechanical and electromechanical operation of one preferred cycle ergometer can be found in the above cross-referenced and oft-cited Boyd application and to the extent necessary, such details are deemed incorporated herein by reference.

FIG. 3 shows the bicycle ergometer device represented generally at 38 and including crank 40 and a motor 46, both of which are connected in operable relationship to a flywheel 48. As is notoriously well known, the subject 30 positions himself on a seat as at 50 (FIG. 1) and while gripping handlebars 52, pedals the crank 40. The crank, in turn, is operatively connected to the flywheel 48 which is also operatively connected with the motor 46 which is a reversible, variable speed direct current motor. The motor 46 can be utilized, as needed, as in conjunction with a braking system as described by Boyd, previously cited, to assist or retard the crank 40 with respect to the rotation of the flywheel 48 to achieve, with the input of the subject, any desired workrate.

A tachometer 54 is coupled to the crank so as to reflect the speed at which the pedals are being driven and an electrical signal proportional to speed is developed on line 56 and fed first to an A/D conversion means in the form of digitizing board 58 and thereafter as a first input to a multiplier circuit 60. The second input to the multiplier circuit 60 comes from a load cell 62 which is gimbal mounted relative to the crankshaft 40. The load cell provides a means whereby a signal proportional to the actual torque exerted by the subject at the pedals is developed. This analog signal is applied, via conductor 64, to the digitizing board 58 and thereafter as a second digital input to multiplier module 60.

The multiplier module is effective to multiply the pedal velocity signal, w, with the motor torque, T, with the resulting signal being proportional to work or power measured in watts. That is, the formula for computing the power, P, is:

$$P = T \times W / 84.484$$

where:
P = Power (rate of work) of the patient (watts)
T = Average torque (in-LB)
W = Instantaneous motor velocity (RPM)

The signal proportional to computed power is then applied via 66 through a low-pass filter (not shown) to a first input of a difference amplifier or subtracter circuit 68. The other input to the subtracter circuit 68 comprises a work set-point value at 70 which is obtained from the User Interface Processor (UIP) 42 on line 74 (FIG. 4). Alternatively, the setpoint may be supplied from a cardiopulmonary exercise stress test protocol (see also FIG. 5) on line 76 which may be displayed as at 77. More particularly, the work rate-versus-time protocol previously stored on the machine-readable medium is read by the floppy disc drive or the user interface processor 72 and signals proportional to the instantaneous specified workrate are delivered to the differencing circuit 70 where a computation takes place to determine the difference between the set-point value and the filtered power being developed by the patient as he pedals the ergometer 28 or 38.

A signal proportional to this difference is then applied, via either 78 or 80, as applicable, to a motor control device 82 which, in the case of conductor 80, modulates the current into the armature winding of the DC motor 46 and, in the case of 78, with reference to the Boyd device, reverses the motor to cause a braking action to resist the pedal motion.

It can be seen, then, that the actual power delivered by the patient is compared to the power demanded by the protocol and the difference is measured. If this difference be positive, the motor 46 is driven such that the torque at the pedal is reduced until the difference is zero. If the difference be negative, the torque at the pedal is increased until the difference is zero. The addition or reduction in torque is accomplished by increasing or decreasing the current, $I_A$, being supplied to the motor 46 which is normally being driven in the direction which the subject is pedaling or reversing the motor to engage a brake band, as described in the co-pending Boyd application, to produce the resisting torque. It is important to note that because of the manner in which the strain gauge or load cell 62 is positioned relative to the pedal crank 40, the actual torque produced by the subject at the pedal is the quantity being measured, and not the torque on a flywheel as in conventional bicycle ergometers.

If the rpm input by the subject is generally out of the range readily corrected by the system, a differentiating device 84 will signal a display LED system at 86 to display the information to the subject using the direct display device 44 (FIG. 4). FIG. 4 further depicts the programming hardware associated with the preparation of the data key or floppy disc containing the protocol for the exercise regimen of the subject. It represents a further flow chart representation of the schematic system shown in FIG. 1. Thus, during operation of the bicycle ergometer 38, optional sensors as at 94 may be utilized to sense various physiological dependent variables of the subject. A remote heart rate receiver 96 may be provided together with a keypad 88 for entry of data by the subject as desired or required during the exercise protocol. A printer 90 is further provided connected to the UIP 72 via 92 to print out reports or any other data requested by the protocol or the subject himself through the keypad.

Because the subject is made to work against a DC motor as a load, a mode of operation is provided in which the pedals are advanced by driving the motor forward upon the detection of any torque applied at the pedals. By seeking to "run away" from torque, a zero ergometric workload may be achieved. This is a major benefit to clinicians in medical applications, for example, who are required to test pediatric patients or patients with heart and lung disease and to whom a power requirement of even 25 watts may be too strenuous. Those prior art ergometers which employ a mechanical flywheel and friction brake arrangement exhibit an internal mechanical resistance and inertia which imparts a load of anywhere from 15 to 40 watts as a no-load setting.

The ergometer of the embodiment illustrated in the Figures, then, is characteristic of those compatible with the practice of the method of the present invention. It is designed to deliver accurate power to the patient starting at 0 watts to approximately 500 watts over a range of pedal speeds from 40 rpm to 125 rpm. More importantly, however, the device has the ability to measure the actual workrate of the subject and the further capability to assist or retard that workrate in order to achieve a protocol setpoint.

Another advantage of the particular ergometer design used in carrying out the method of the present invention is that it provides a very rapid response to workload changes, thus allowing a close tracking of a prescribed work-versus-time profile. With most flywheel ergometers, a rapid response is not obtainable because such ergometers cannot immediately adjust to patient load, but only to flywheel load. The rapid response afforded by the preferred ergometer allows workrate-dependent cardiac and pulmonary variables, such as oxygen uptake kinetics, $O_2$ pulse to be studied on a real-time basis. In particular, the response time needed to achieve a change in actual workrate upon a change in the workrate set-point may be less than three seconds.

During the course of an exercise session, patient physiologic data may be gathered by instrumentation module 94 having electrodes or probes adapted to be attached to the patient so as to feed information about the patient's physiologic state to the UIP 72 for recording on a machine-readable medium, e.g., a data key. The instrumentation module 94 may typically comprise a pulse oximeter for measuring heart rate and oxygen saturation. Using the key pad 88, the patient, at pre-established time intervals, may enter his own subjective rate of perceived exertion (RPE) as a psychological response.

It is important to understand and appreciate that the invention involves much more than the development and use of an exercise protocol. The present invention encompasses an unique philosophical approach to the field of physical rehabilitation and conditioning in which the intensity and duration of the workouts become independent variables of the protocol and the measured physiological and psychologic responses are the dependent variables. It is the changes in the dependent variables that are noted with respect to repetition of the same protocol that are used to evaluate efficacy and as a basis for modifications.

Figure 2:
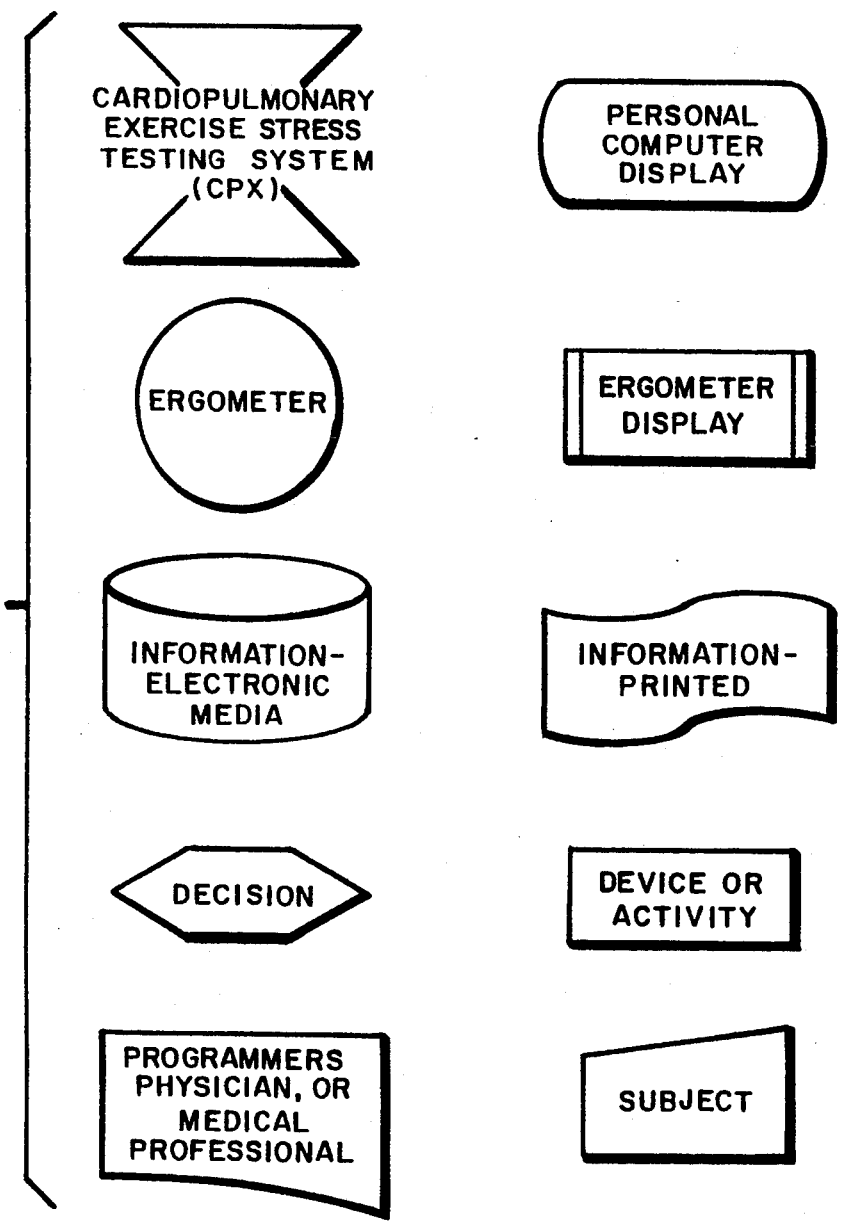
FIG. 2 is a key to symbols used in FIGS. 3, 4, 5, 6A and 6B.
Figure 5:
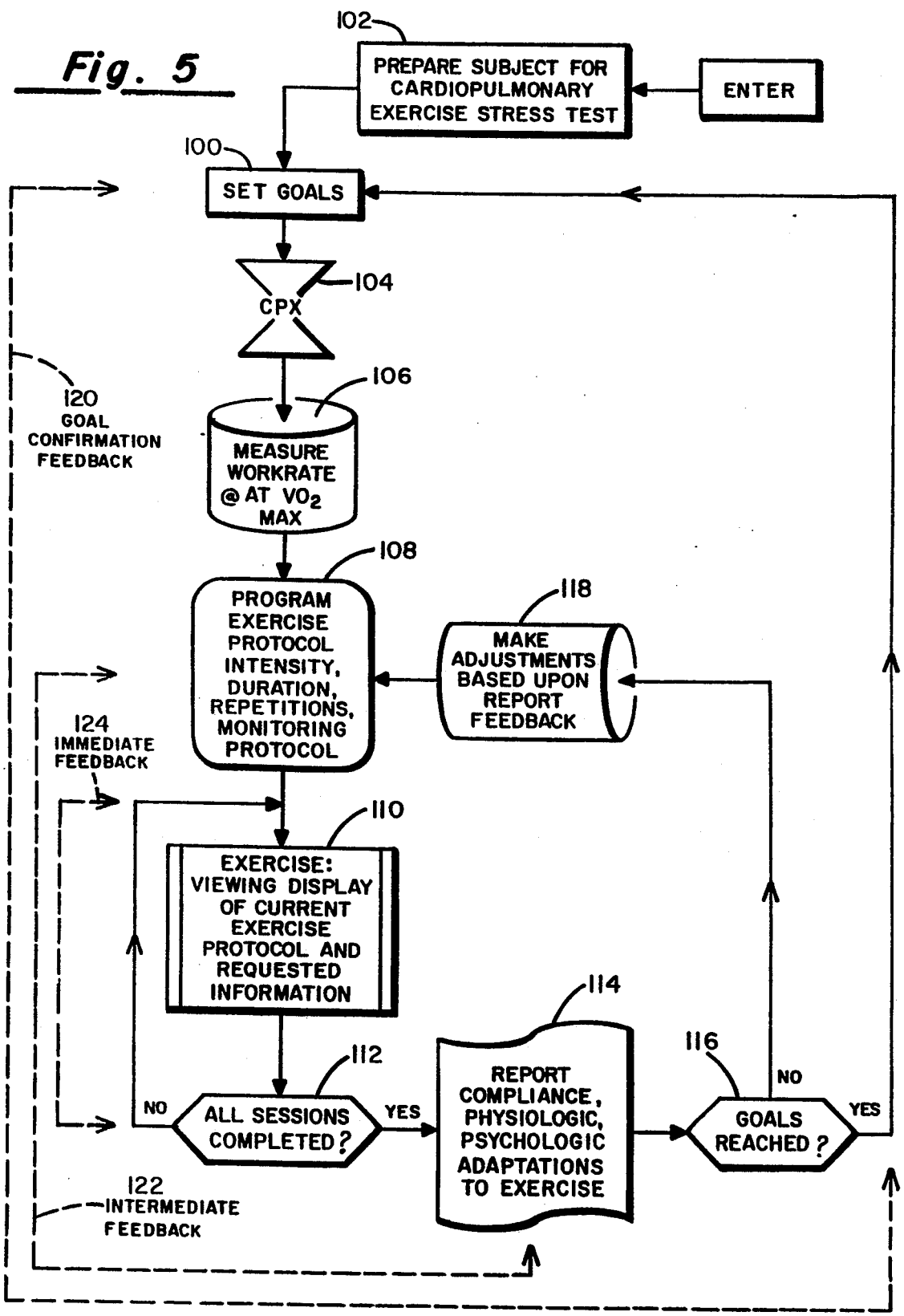
FIG. 5 is a process flow chart of the general method of the invention.
Figure 6A:
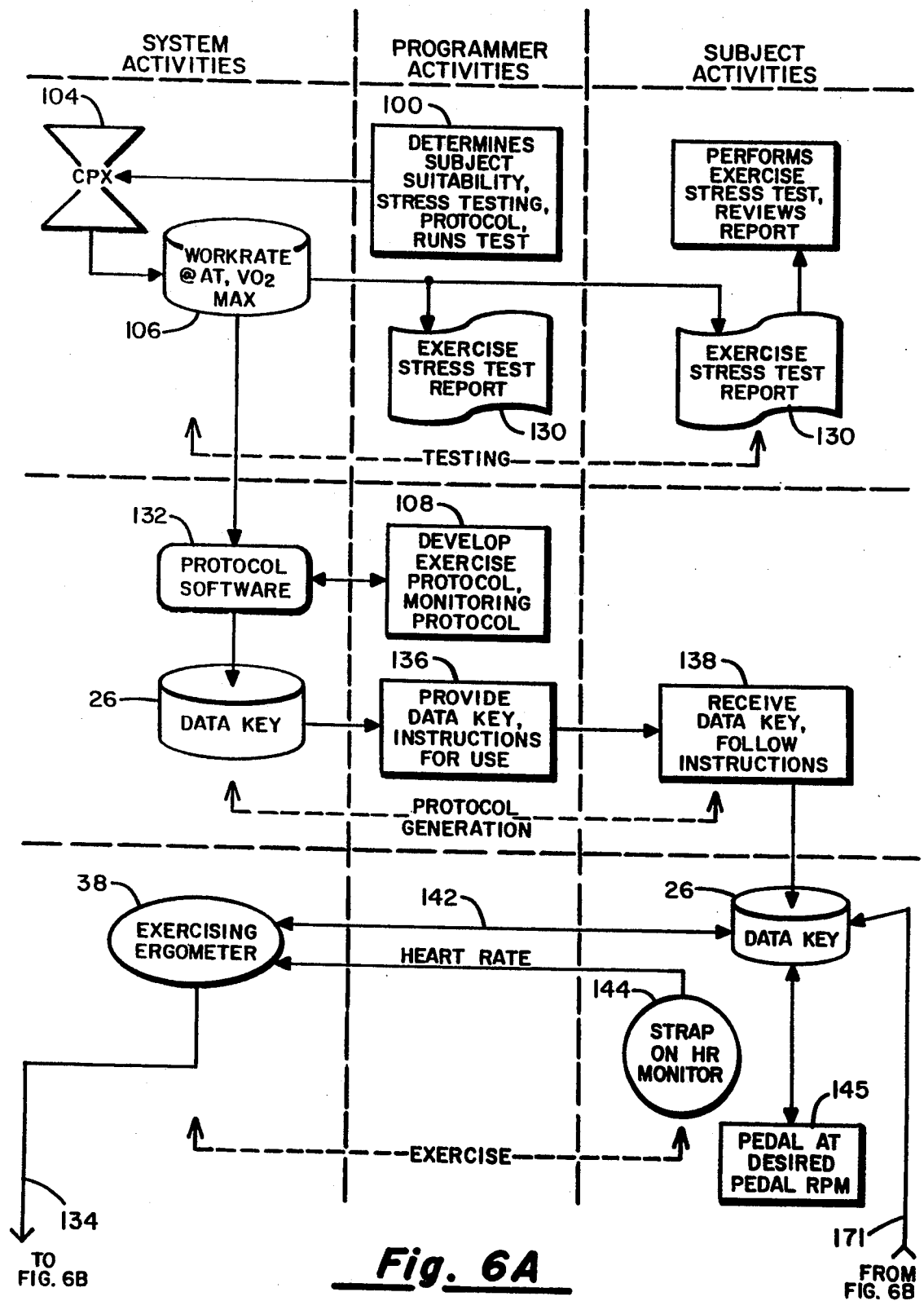
FIGS. 6A and 6B are flow charts showing details of the method of FIG. 5.
Figure 6B:
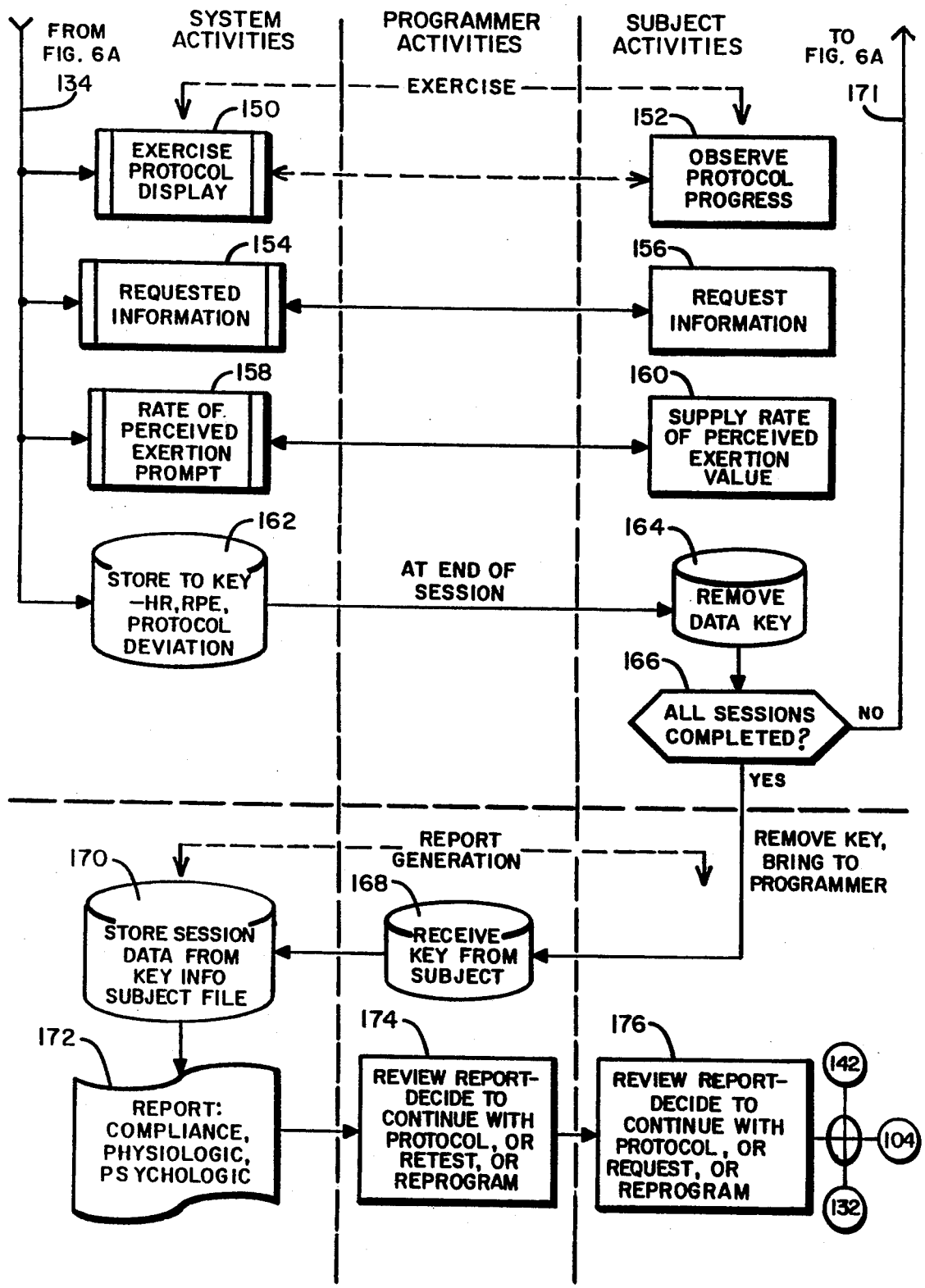

FIGS. 4, 5, 6A and 6B illustrate such an implementation. FIG. 2 represents a self-explanatory key to facilitate the interpretation of FIGS. 3, 4, 5, 6A and 6B. FIG. 5 represents an overview flow chart of the method of the invention including information feedback loops and FIGS. 6A and 6B show a more detailed flow chart of the testing, protocol generation, exercise and reporting functions. This is done in terms of the actor involved and illustrates interaction between actors where indicated.

FIG. 5 is intended to illustrate generally one successful implementation of the method espoused by the invention. The potential subject is first evaluated by the medical professional (programmer) to determine suitability for undergoing stress testing and if such is feasible, a stress testing protocol is determined as at 100 in FIG. 5. The subject is prepared for the test at 102 and the test is conducted using a cardiopulmonary exercise stress testing system (CPX) at 104. The cardiopulmonary exercise stress test is performed to determine that subject's exercise tolerance, as defined by anaerobic threshold and $VO_2$ max. The workrates at which these physiological limitations occur are noted at 106 and are used as the basis for defining the exercise protocol at 108, in terms of duration and intensity. As shown in the testing section of FIG. 6A, an exercise stress test report is generated at 130 and is reviewed both by the programmer and subject prior to the development of the exercise protocol.

Figure 9:
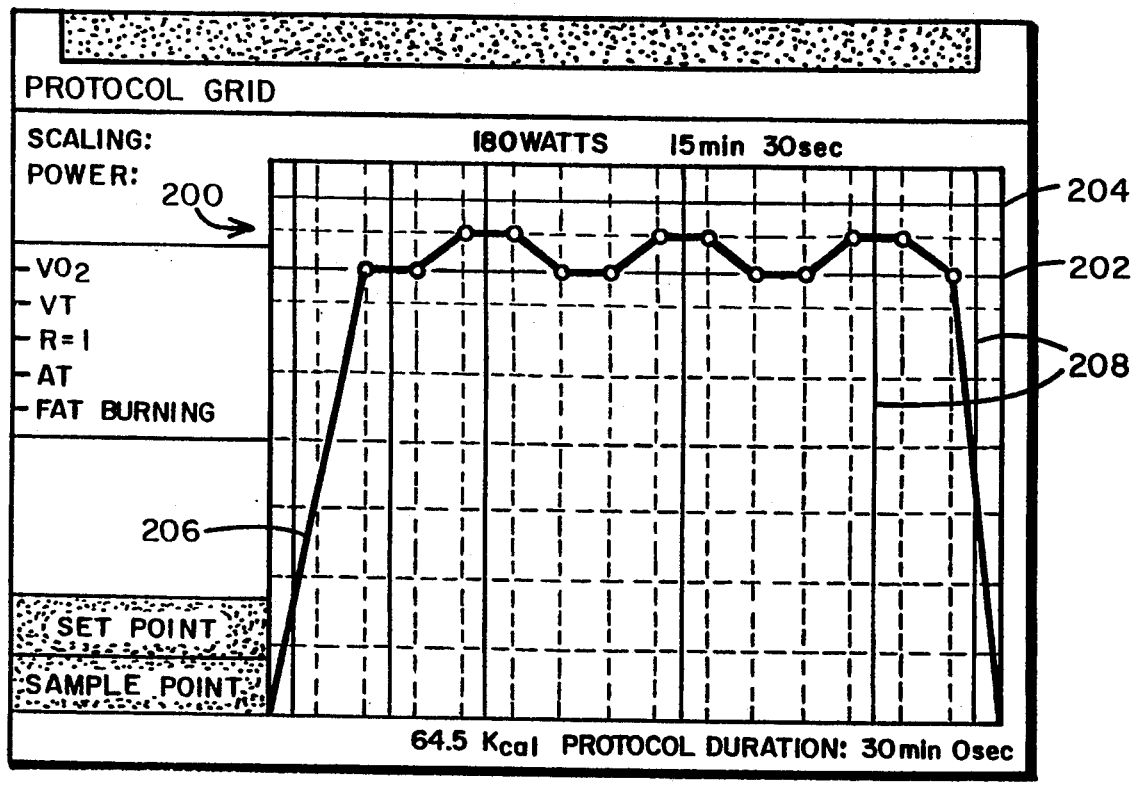
FIG. 9 illustrates a graphic display used to develop or generate a protocol.

A very important aspect of the invention includes the use of a graphical interface to develop an exercise protocol and an off-line monitoring protocol enabled by a very versatile personal computer (PC) compatible resident software program. As shown in FIG. 9, the program provides a graphical user interface to facilitate the development of an exercise protocol and an off-line monitoring protocol. It can be used to display a graph of workrate vs. time, which can be scaled in either dimension. In addition, both a visible grid as at 200 and a snap-to grid can be implemented to simplify the formation of the exercise protocol, which is essentially a workrate vs. time plot.

The exercise protocol is determined by the exercise programmer, either a physician or other medical professional such as an exercise physiologist. After the programmer has entered the requested information on the subject, two horizontal lines appear on the graph representing the workrates, the lower level 202 may, for example, represent the anaerobic threshold (AT) and the upper level 204 representing the $VO_2$ max (if measured). If no measurements of the variables have been made, they can be determined by computation, using well-known prediction equations such as those developed by Karlman Wasserman et al. These horizontal lines can be thought of as defining the "training window". This then provides enough pertinent information to design the exercise protocol for the subject.

The workrates, of course, are simply guidelines for determining exercise intensity only and not duration. The actual protocol reflects the training, experience, and initial impression of the subject by the programmer. The protocol is formed by simply locating a cursor, moved by a mouse for example, rubber banding a line to a point on the graph and "clicking" the mouse at each desired location. In this manner, as shown on line 206 in FIG. 9, a protocol of any duration or complexity can be easily formed. In addition, the software enables computation of the caloric energy expenditure required by the protocol by first calculating the area enclosed by the exercise protocol (line 206), multiplying this area calculation (work) by the appropriate conversion constant to yield kilocalories, and this value may be displayed in a window on the graph.

Once the protocol is defined, the next step is to select when a monitored variable is to be sampled. As a minimum, HR and Rate of Perceived Exertion (RPE) should be sampled. The system is designed, however, so that other variables can also be sampled such as blood pressure (BP) or oxygen saturation. This selection is implemented by locating a vertical bar 208, which moves in relation to movements by the mouse, at the desired time location and again "clicking" the mouse. This is done for each sample point.

It is an important aspect of the invention that, once generated, the resulting exercise protocol and monitoring protocol at 132 (FIG. 6A) are then recorded into the database of the subject on the system disc of the PC and onto a portable form of recording media, such as a floppy disc 22 or data key as at 26 (FIG. 6A). Once the protocol is recorded onto the data key, it can be transported by the subject or sent to the subject for use anywhere in the world with any remote ergometer 38 (as at 136, 138 in FIG. 6A) suitably equipped with a special-purpose microcomputer, programmed to be able to read the encoded information on the data key. This may be a PC as at 12 in FIG. 1 or a far less expensive, less sophisticated microcomputer based system. Upon inserting the data key into the key reader 24 on the ergometer, the microcomputer reads the encoded information into its memory and instructs the subject to begin pedaling.

The ergometer 38 itself is under control of its own separate microcontroller (PC) or other microcomputer controlled system 42 (FIG. 1) which monitors the torque and pedal speed of the subject, computes workrate, and adjusts the braking force to achieve a defined workrate. It also signals the subject to either increase or decrease pedal speed, if the observed pedal speed of the subject is out of the range of speed which the ergometer's braking control system was designed to accommodate. The relevant microcomputer supplies the information defining what the workrate should be at any point in time, according to the generated exercise protocol which was transferred via the data key 26 as on line 142.

While the subject is exercising, as at 110 (FIG. 5), information on line 134 will be exchanged and stored back onto the data key at 162 (FIG. 6B). This information represents subject compliance, physiologic adaptation at 158, such as heart rate at 144, and psychological adaptation; and this information is stored uniquely for each exercise session. Compliance data is stored in terms of actual workrate deviation. Since the ergometer microcontroller is continually measuring the actual workrate of the subject, this information is passed to the microcomputer, which is programmed to store any workrates that are lower than a predefined percentage of that of the exercise protocol at the time. Because the ergometer microcontroller is designed in such a way that setpoint cannot be exceeded, except for very brief periods of time, positive deviations are not recorded. To save memory, only the start time and end time of a negative deviation is recorded.

The microcomputer also has, as an integral part of its design, a commercially available receiver for a wireless heart pulse signal. The microcomputer is continuously monitoring this incoming pulse signal, and heart rate is computed using a sliding 10-beat average of pulse interval time. As controlled by the monitoring protocol, the heart rate observed at the sample time is stored onto the data key.

In addition, as further controlled by the monitoring protocol, from time to time messages are displayed on the display of the ergometer. As shown in FIG. 6B, the exercise protocol may be displayed and observed by the subject as at 150 and 152. Information may be requested either by the programmer or the subject as at 154 and 156. A further message asks the subject to enter RPE at 158, the rate of perceived exertion (FIG. 6B). The subject then presses the appropriate key on the keyboard of the ergometer, and the RPE value selected at 160 is stored onto the data key as at 162. The actual value of RPE has no specific meaning, other than to indicate how a particular subject "feels" at a given time and exercise intensity. Hence, it is deemed a psychological variable.

Each time the subject exercises as at 112, 145 (FIG. 6A) using the same protocol, the monitored variables are recorded and stored onto a new record on the data key at 162 (FIG. 6B). The end result is a series of records which contain the recorded independent variables under identical conditions (workrate and elapsed time) for a series of days. With these records, a profile can be developed by the programmer for use as feedback to either the programmer of subject at any time. Such profiles are illustrated in FIGS. 7A, 7B, 8A and 8B.

With further reference to FIG. 6B, the records are in the removable data key at 164 upon completion of all program sessions at 166 which can be removed and given to the programmer as at 168 and stored in the subject's file at 170. Session count is kept on the data key via line 171. The feedback may be obtained in the form of a detailed printed report of the recorded data 172, to be reviewed and evaluated by the programmer at 174, 176. The program report may be generated using software comprising another PC resident program.

The function of the report generating program at 114 (FIG. 5) is to read the stored records from the data key and to produce three graphical reports. The first report (not shown) displays the compliance of the subject by plotting those sessions during which negative deviations in workrate from that of the exercise protocol occurred. If no deviations were noted, the subject has complied completely.

The second report (FIG. 8B) displays a plot of HR at each sample point for each successive session. The three-dimensional plot is arranged so that the last exercise session is viewed in the frontal plane of the graph, while the first exercise session is viewed, partially hidden by data representing intermediate sessions, in the rear plane of the graph. The plot shows a definite reduction in required heart rate from day 1 to day n. This is because as the subject experiences a positive or beneficial physiologic training effect, the heart rate should be lower at any particular sample point.

Figures 7A, 7B:
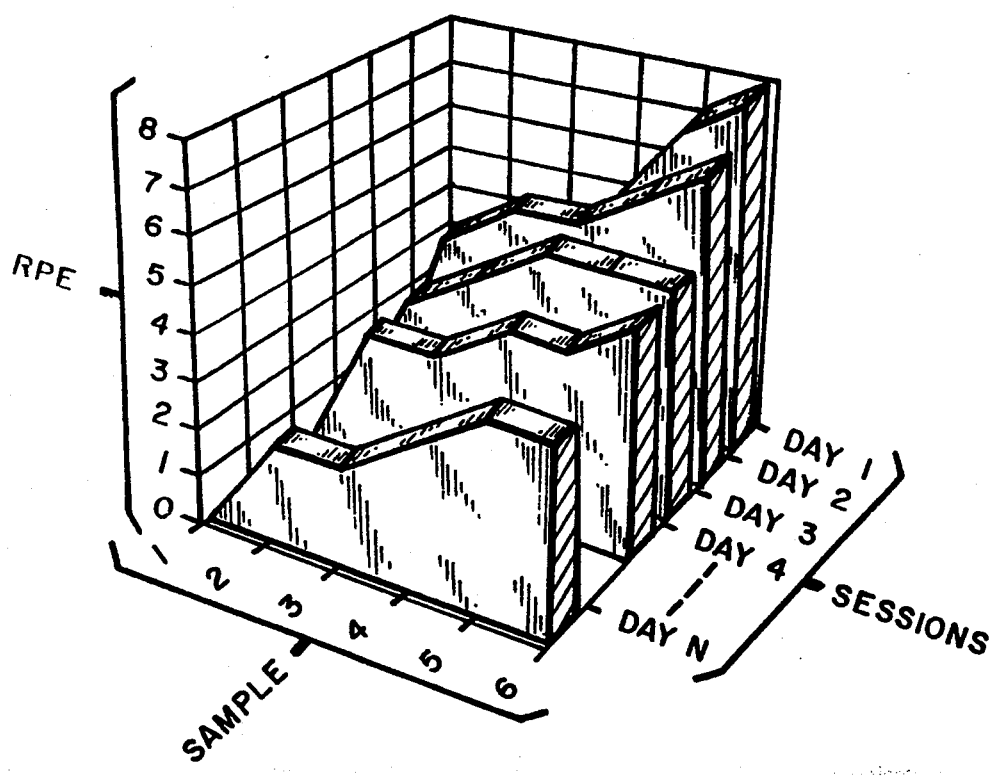
FIGS. 7A and 7B show the effect of a program of the invention on the rate of perceived exertion.
Figures 8A, 8B:
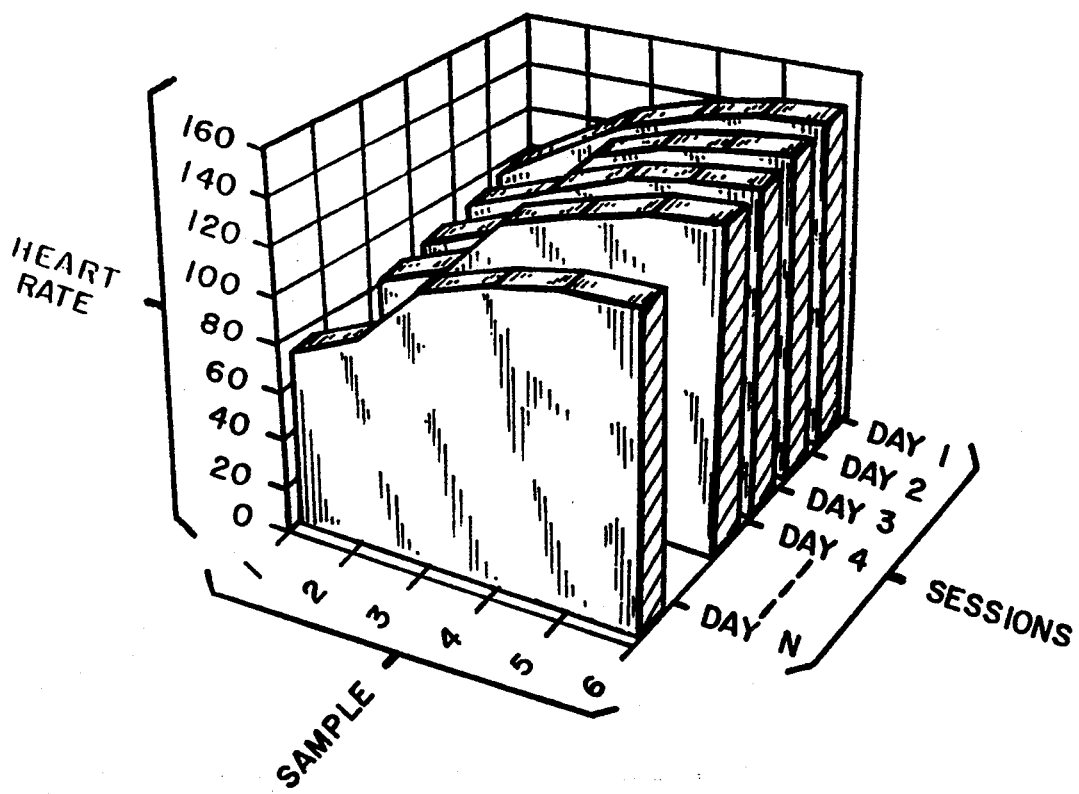
FIGS. 8A and 8B illustrate the effect of a program of the invention on heart rate.

The third graph depicted in FIG. 7B is that of RPE. As was the case with the HR of the subject, as the subject experiences a positive psychological training effect, the RPE should also be lower because the subject "feels" better about exercising at any given intensity.

This information, in combination, can then be used by the programmer and the subject to alter the exercise protocol as at 118. Depending upon the rate and/or magnitude of the improvement at 116, three possible situations can arise:

A. Slight change—Resume the exercise training program using the same protocol, or abandon training entirely.

B. Moderate change—Increase the duration of the exercise protocol but keep the intensity of the protocol the same.

C. Dramatic change—Repeat the cardiopulmonary exercise stress test. Reset the "training window" to a higher workrate to reflect the increase in exercise tolerance which resulted from the exercise training program to date. Redesign the exercise protocol and monitoring protocol. Begin a new phase of training.

As can be seen, in FIG. 5, the system is a closed loop system employing an outer long-term feedback loop 120 (intensity regulation based upon cardiopulmonary stress test measurements), an inner intermediate feedback loop 122 (appropriateness of intensity regulation based upon compliance, physiological and psychological measurements), and an immediate feedback loop 124 (prescribed vs. actual exercise protocol). Feedback is provided periodically in the form of reports using the measurements. Control is maintained co-dependently as a result of conscious decisions made by the programmer and the subject using the reports and measurements.

In accordance with the invention, utilization of this method reduces the costs of providing exercise training in many ways including:

A. The method provides an outcome based strategy for producing a training effect in the shortest period of time.

B. It provides an outcome based report for use by third party payers to reimburse health care providers for their services.

C. The use of the inner loop, employing essentially a no-cost monitoring capability, reduces the use of the more expensive outer loop which requires retesting.

D. Health providers can improve the cost effectiveness of their training programs as it enables expanding the numbers of subjects served without increasing staff or by reducing staff for those program which experience no increase in subjects served.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

I claim:

1. A method of automating a process for conditioning or rehabilitating a subject utilizing an aerobic exercise training protocol based on an aerobic threshold method of exercise training performed on a polyarticular aerobic exercise device, comprising the steps of:

(a) creating a first polyarticular aerobic exercise protocol and storing said first protocol on a transportable memory device, said first protocol using a target exercise intensity (workrate) as the controlling variable, wherein the intensity and duration are related to at least one parameter selected from maximum aerobic capacity ($VO_2$ max) and anaerobic threshold (AT) of the subject;

(b) creating a first monitoring protocol and storing said first monitoring protocol on said memory device, said first monitoring protocol being dedicated to operate during performance of said first aerobic exercise protocol and further defining monitoring and sampling intervals for obtaining real-time data from the subject indicative of non-controlling physiological variables selected from oxygen consumption ($VO_2$), carbon dioxide production ($VCO_2$), ventilation (VE), heart rate (HR) and blood pressure (BP) and optionally psychological variables selected from the rate of perceived exertion (RPE) and compliance with the exercise protocol during each such repetitive execution of the exercise protocol;

(c) transferring the transportable memory device to an aerobic exercise device, said device being automated for operation by the transportable memory device, said device including means for measuring actual power delivered by the subject and controlling the level of subject input power required to achieve said target intensity in an automated manner;

(d) wherein the subject reproduces the exercise protocol using said aerobic exercise device through at least a first program, a program comprising repetitive execution of said first aerobic exercise protocol in a series of successive sessions;

(e) obtaining real-time data of one or more of said non-controlling physiological variables according to said first monitoring protocol during each repetitive execution of said first aerobic exercise protocol;

(f) optionally monitoring non-controlling psychological variables during execution of said first aerobic exercise protocol according to said first monitoring protocol;

(g) wherein said real-time data obtained in accordance with said monitoring protocol remains independent from the operation of said exercise device;

(h) causing selected real-time data obtained to be stored in said memory device according to said first monitoring protocol; and (i) using changes in one or more measured non-controlling physiological and psychological variables observed over the course of said several sessions of said first program based on data stored in said memory device to evaluate progressive effectiveness of the protocol.

2. The method of claim 1 wherein the aerobic exercise device includes associated computer driven subject interface means including graphical display means and wherein the method further comprises the step of providing real-time visual interface with the subject including graphical display data feedback related to the exercise and/or monitoring protocol.

3. The method of claim 2 further comprising the step of optionally modifying the first exercise protocol to create additional sequential exercise protocols based on changes in one or more of the monitored non-controlling physiological and psychological variables over said first or another previous program.

4. The method of claim 1 further comprising the step of modifying the first or another previous monitoring protocol.

5. The method of claim 1 wherein the memory device is a transportable, remotely usable recording medium, includes means for receiving, storing and retrieving data and can be used both with a remote independent aerobic exercise device to be operated by the subject to perform the repeated protocols of the program and thereafter by an evaluator to evaluate the progress of the subject.

6. The method of claim 5 wherein the aerobic exercise device includes computer driven subject interface means including graphical display means and wherein the method further comprises the step of providing real-time visual interface with the subject including graphical display data feedback related to the exercise and/or monitoring protocol.

7. The method of claim 2 further comprising the step of monitoring compliance with the exercise protocol by monitoring the actual intensity delivered by the subject in real-time and comparing it to said target intensity at a like time in the exercise protocol.

8. The method of claim 2 including the step of displaying data of one or more of the non-controlling physiological or psychological variables to the subject on a real-time basis.

9. The method of claim 7 including the step of providing human readable output indicative of compliance with the exercise protocol by displaying in real-time a comparison of the intensity delivered by the subject in relation to the target intensity at a like time in the protocol.

10. The method of claim 2 wherein the subject interface means includes provision for real-time interaction with the subject and wherein the method includes the further step of real-time interrogation of the subject.

11. The method of claim 10 wherein the step of real-time interrogation further include, requesting subjective information of the subject.

12. The method of claim 11 including interrogation of the subject related to the subject's rate of perceived exertion (RPE).

13. The method of claim 1 wherein said target exercise intensity value is logically related to AT and $VO_2$ max.

14. A computer graphic method of developing and modifying a polyarticular aerobic exercise training protocol using an anaerobic subject threshold method of exercise training and for developing and modifying a monitoring protocol for conditioning or rehabilitating a subject using dedicated software that runs on a personal computer, the protocol to be performed on a mechanized, programmable computer-controlled polyarticular aerobic exercise device, said device including means for measuring intensity of exercise by directly measuring the actual power delivered by the subject and means for controlling the level of subject input power required to achieve a target workrate in an automated manner, comprising the steps of:

(a) providing a graphic display in the form of a protocol grid of an exercise workrate v. time plot;

(b) displaying the value of a training window defined by upper and lower workrates in which maximum aerobic capacity ($VO_2$ max) is the upper window limit and anaerobic threshold (AT) is the lower window limit as indicia on the graphic display to act as guidelines for programming the exercise intensity of the exercise training protocol;

(c) using the graphical display to create and edit a proposed exercise training protocol of any desired complexity based on aerobic exercise duration and intensity as the controlling variable, and including a monitoring protocol having predetermined sampling intervals for recording non-controlling physiological variables selected from the group consisting of oxygen consumption ($VO_2$), carbon dioxide production ($VCO_2$), ventilation (VE), heart rate (HR) and blood pressure (BP), optionally non-controlling psychological variables selected from the group consisting of rate of perceived exertion (RPE) and compliance with the exercise protocol; and (d) transferring to and storing a programmed aerobic exercise and monitoring protocol together with subject user instructions on a transportable, machine readable recording medium capable of interfacing with an output means and receiving and storing additional data.

15. The method of claim 14 wherein the protocol further includes real-time subject interface aspects.

16. The method of claim 14 wherein the graphic display is one in which the vertical axis depicts intensity level and the horizontal axis depicts time duration.

17. The method of claim 15 wherein the recording medium is a floppy disc.

18. The method of claim 15 wherein the recording medium is a data key.

19. The method of claim 14 wherein the exercise protocol is developed and edited on the protocol grid using a cursor and rubber banding technique.

* * * * *